United States Patent [19]
Faris

[11] Patent Number: 6,129,911
[45] Date of Patent: Oct. 10, 2000

[54] LIVER STEM CELL

[75] Inventor: Ronald A. Faris, Providence, R.I.

[73] Assignee: Rhode Island Hospital, A LifeSpan Partner, Providence, R.I.

[21] Appl. No.: 09/113,774

[22] Filed: Jul. 10, 1998

[51] Int. Cl.[7] .............................. A01N 63/00; A01N 65/00
[52] U.S. Cl. ........................... 424/93.7; 435/1.1; 435/325; 424/93.1
[58] Field of Search ................................. 424/93.7, 93.1; 435/325, 1.1, 405

[56] References Cited

U.S. PATENT DOCUMENTS

| | | | |
|---|---|---|---|
| 5,460,964 | 10/1995 | McGlave et al. | 435/240.21 |
| 5,532,156 | 7/1996 | Talbot et al. | 435/240.2 |
| 5,548,065 | 8/1996 | Lemischka | 530/388.22 |
| 5,559,022 | 9/1996 | Naughton et al. | 435/240.2 |
| 5,576,207 | 11/1996 | Reid et al. | 435/240.2 |
| 5,861,313 | 3/1999 | Pang et al. | 435/347 |

FOREIGN PATENT DOCUMENTS

| | | | |
|---|---|---|---|
| WO 93/03142 | 2/1993 | WIPO | C12N 5/08 |
| WO 94/08598 | 4/1994 | WIPO | A61K 35/407 |

OTHER PUBLICATIONS

Bloom et al., The textbook of Histology, Twelfth Edition; Chapman & Hall, New York, Sep. 1995.
Sirica et al., Pathobiology 58:44–64, Jun. 1990.
Yang et al., Gastroenterology 104:840–852, Mar. 1993.
Yasui et al., Hepatology 25:329–334, Feb. 1997.
Anderson, Nature 392:25–30, Apr. 1998.
Verma et al. Nature 389:239242, Sep. 1997.
Debeva et al. Proceedings of the Society for Experimental Biology and Medicine 204:242–252, Dec. 1993.
Agelli et al., "Flow Cytometry and Monoclonal Antibodies Identify Normal Liver Cell Populations Antigenically Related to Oval Cells", Eur. J. Histochem 39:175–182, 1995.

Agelli et al., "Putative Liver Progenitor Cells: Conditions for Long–Term Survival in Culture", The Histochemical Journal 29:205–217, 1997.

Bisgaard et al., "Keratin 14 Protein in Cultured Nonparenchymal Rat Hepatic Epithelial Cells: Charac terization of Keratin 14 and Keratin 19 as Antigens for the Commonly . . . ", Molecular Carcinogenesis 7:60–66, 1993.

Brill et al., "Hepatic Progenitor Populations in Embryonic, Neonatal, and Adult Liver[1] (43662)", Hepatic Proc. Soc. Exp. Biol. Med. (U.S.), 204(3):270–279, 1993.

Gilles et al., "Immunophenotypic Characterization of Human Fetal Liver Hematopoietic Stem Cells During the Midtrimester of Gestation", Am. J. Obstet. Gynecol. 177(3):619–625, 1997.

Grisham et al., "Isolation, Culture, and Transplantation of Rat Hepatocytic Precursor (Stem–Like) Cells (43663)", Proc. Soc. Exp. Biol. Med. (U.S.), 204(3):270–279, 1993.

Hixson et al., "Antigenic Phenotypes Common to Rat Oval Cells, Primary Hepatocellular Carcinomas and Developing Bile Ducts", Carcinogenesis 18:1169–1175, 1997.

Lemmer et al., "Isolation and Culture of Hepatic Stem Cells From Human Foetal Liver: A Preliminary Report", Hepatology, I–56 Iasl Abstracts 23(1):157P,1996.

(List continued on next page.)

*Primary Examiner*—Bruce R. Campell
*Assistant Examiner*—Joseph Woitach
*Attorney, Agent, or Firm*—Mintz, Levin, Cohn, Ferris, Glovsky and Popeo, PC; Ingrid A. Beattie

[57] ABSTRACT

The invention provides a primary liver stem cell and a cell doublet consisting of a hepatocyte and the stem cell, both of which are derived from normal liver tissue. Methods of isolating the cells, genetically altering the cells, and using the cells for transplantation are also within the invention.

50 Claims, 4 Drawing Sheets

OTHER PUBLICATIONS

Novikoff et al., "Stem Cells and Rat Liver Carcinogenesis: Contributions of Confocal and Electron Microscopy" The Journal of Histochemistry & Cytochemistry 46(5):613–626, 1998.

Pack et al., "Isolation, Biochemical Characterization, Long-Term Culture, and Phenotype Modulation of Oval Cells from Carcinogen-Fed Rats", Experimental Cell Research 204:198–209, 1993.

Sell et al., "Normal Liver Structure and Function", Liver Stem Cells, Chapter 3, pp. 83–116, 1997.

Sirica et al., "Isolation, Culture, and Transplantation of Intrahepatic Biliary Epithelial Cells and Oval Cells[1]", Pathobiology 58:44–64, 1990.

Sirica et al., "Isolation and Partial Characterizations of Oval and Hyperplastic Bile Ductular Cell–enriched Populations from the Livers of Carcinogen and Noncarcinogen–treated Rats[1]", Cancer Res. 44(8):3454–3466, 1984.

Travis, "The Search for Liver Stem Cells Picks Up", Science 259:1829, 1993.

Yang et al., "Characterization of a Mature Bile Duct Antigen Expressed on a Subpopulation of Biliary Ductular Cells but Absent from Oval Cells", Hepatology 18(2):357–366, 1993.

Yang et al., "Long–Term Culture and Characteristics of Normal Rat Liver Bile Duct Epithelial Cells", Gastroenterology 104:840–852, 1993.

Yasui et al., "Isolation of Oval Cells From Long–Evans Cinnamon Rats and Their Transformation Into Hepatocytes in Vivo in the Rat Liver", Hepatology 24(2):329–334, 1997.

M. Alison, "Liver stem cells: a two compartment system", Current Opinion in Cell Biol., 10:710–715, 1998.

Alison et al., "Wound healing in the liver with particular reference to stem cells", Phil. Trans. R. Soc. Lond. B, 353:877–894, 1998.

Lemire et al., "Oval cell proliferation and the origin of small hepatocytes in liver injury induced by D–galactosamine", Am. J. of Path., 139:535–552, 1991.

S. Sell, "Is there a liver stem cell?", Cancer Res., 50:3811–3815, 1990.

Tian et al., "The oval shaped cell as a candidate for a liver stem cell in embryonic, neonatal and precancerous liver: identification based on morphology and pyruvate kinase isoenzyme expression", Histochem. Cell. Biol., 107:243–250, 1997.

LIVER STEM CELL

BACKGROUND OF THE INVENTION

The invention relates to the cell-mediated treatment of liver disease.

Patients who suffer from severe, irreversible liver disease for which other medical and surgical treatments have failed are often candidates for liver transplantation. In children, the most common indications are biliary atresia, a condition which leads to distortion of bile ducts and liver cirrhosis and genetically transmitted metabolic disorders which may lead to hepatic failure and/or cirrhosis. Adult suffering from nonalcoholic or alcoholic cirrhosis as well as liver cancer may be candidates for transplantation.

The existence of an adult liver stem cells remains the subject of controversy. However, stem cells which differentiate into functional mature hepatocytes to reconstitute a diseased liver may be an alternative approach to whole organ transplantation for the treatment of certain liver diseases.

SUMMARY OF THE INVENTION

The invention provides primary liver stem cells which can be used to treat degenerative liver diseases or inherited deficiencies of liver function, e.g., those characterized by production of a mutant protein or by the misregulation of protein expression that results in liver dysfunction. The stem cells may be multipotential, e.g., the cells can differentiate into hepatocytes or bile ductal cells, or they may be pre-committed to differentiating into hepatocytes. The invention also provides a method for isolating and utilizing stem cells and cell doublets not only for hepatic transplantation but also for gene therapy and as the biological component of liver assist devices.

Accordingly, the invention includes a primary liver cell cluster containing a liver stem cell and a hepatocyte or an isolated primary liver stem cell. By "stem cell" is meant an undifferentiated cell that differentiates into a mature functional hepatocyte or bile duct cell. "Facultative" liver stem cells (FLSC) require a stimulus to proliferate. For example, FLSC proliferate in response to stress or injury such as exposure to a carcinogen. Stem cells are not fully differentiated and retain the ability to proliferate under conditions which differentiated liver cells normally do not proliferate, e.g., following exposure to chemical carcinogens. By "cell cluster" is meant a group of at least two associated cells. Preferably, the cluster contains less than 10 cells, more preferably less than 5 cells. Typically, the isolated cell clusters contain between 2 and 5 cells per cluster. Most preferably, the cluster is a cell doublet, i.e., a cluster containing two cells, or a cell triplet, i.e., a cluster containing three cells. Within the cluster, at least two of the cells are joined by a desmosomal junction. By "normal" liver tissue is meant tissue that is noncancerous and uninfected by pathogenic microorganisms.

The stem cell is distinguished from and can be separated from other undifferentiated or partially differentiated liver cells, e.g., oval cells, by virtue of its association with a hepatocyte. The hepatocyte and stem cell of the doublet are joined by desmosomal junctions. The stem cell is preferably a pre-oval cell and is distinguished from oval cells by the tight association with a hepatocyte and lack of detectable expression of an oval cell marker such as OC2. Preferably the stem cell expresses the marker OV6. The stem cell may also express a bile duct cell marker such as a cytokeratin, e.g., cytokeratin 19. Other cell surface markers such as an extracellular matrix marker such as laminin, a desmosomal glycoprotein such as desmoplakin I, a liver cell adhesion molecule such as cell-cell adhesion molecule (CCAM), a carcinoembryonic antigen (CEA), dipeptidyl peptidase-4, a bile duct marker on oval cells such as $\gamma$-glutamyl transpeptidase ($\gamma$GT), Very Late After Activation (VLA)-2, VLA-3, VLA-5, or VLA-6 may also be expressed.

Isolated liver cell clusters and isolated stem cells may be obtained from fetal, pediatric, or adult liver tissue. Preferably, the cells are obtained from adult liver tissue rather than fetal tissue. The cells may differentiate into mature functional hepatocytes or mature bile duct cells. Preferably, the stem cells differentiate into mature functional hepatocytes, i.e., hepatocytes characterized by liver-specific differentiated metabolic functions, e.g., the expression of albumin, CCAM, glucose-6-phosphatase, $\alpha_1$-antitrypsin, or P450 enzyme activity.

The stem cells may be genetically-altered by the introduction of heterologous DNA. A genetically-altered stem cell is one into which has been introduced, by means of recombinant DNA techniques, a nucleic acid encoding a polypeptide. The DNA is separated from the 5' and 3' coding sequences with which it is immediately contiguous in the naturally occurring genome of an organism, e,g., the DNA may be a cDNA or fragment thereof. In some cases, the underlying defect of a pathological state is a mutation in DNA encoding a protein such as a metabolic protein. Preferably, the polypeptide encoded by the heterologous DNA lacks a mutation associated with a pathological state. In other cases, a pathological state is associated with a decrease in expression of a protein. A genetically-altered stem cell may contain DNA encoding such a protein under the control of a promoter that directs strong expression of the recombinant protein. Such cells, when transplanted into an individual suffering from abnormally low expression of the protein, produce high levels of the protein to confer a therapeutic benefit. For example, the stem cell contains heterologous DNA encoding a metabolic protein such as ornithine transcarbamylase, arginosuccinate synthetase, glutamine synthetase, glycogen synthetase, glucose-6-phosphatase, succinate dehydrogenase, glucokinase, pyruvate kinase, acetyl CoA carboxylase, fatty acid synthetase, alanine aminotransferase, glutamate dehydrogenase, ferritin, low density lipoprotein (LDL) receptor, P450 enzymes, or alcohol dehydrogenase. Alternatively, the cell may contain DNA encoding a secreted plasma protein such as albumin, transferrin, complement component C3, $\alpha_2$-macroglobulin, fibrinogen, Factor XIII:C, Factor IX, or $\alpha_1$-antitrypsin.

The term "isolated" used in reference to a single cell or cell cluster, e.g., a stem cell or stem cell-hepatocyte triplet or doublet, means that the cell or cell cluster is substantially free of other cell types or cellular material with which it naturally occurs in the liver. A sample of stem cells or doublets is "substantially pure" when it is at least 60% of the cell population. Preferably, the preparation is at least 75%, more preferably at least 90%, and most preferably at least 99%, of the cell population. Purity can be measured by any appropriate standard method, for example, by fluorescence-activated cell sorting (FACS).

The invention includes a method of obtaining a sample of liver stem cells by (a) isolating a cell doublet from normal liver tissue, (b) dissociating the stem cell from the hepatocyte, and (c) removing the hepatocyte from the doublet to yield a sample of liver stem cells. The method optionally includes selecting for the expression of other cell markers, such as desmoplakin, OV6, cytokeratin 19, laminin, or CCAM. Preferably, the method includes a step of selecting for cells which lack oval cell marker OC2 expression to enrich for the desired stem cells, i.e., selecting against contaminating bile duct cells which express OC2.

A method of hepatic transplantation is also within the invention. A patient in need of a liver transplant such as one suffering from degenerative liver disease, cancer, or a metabolic disease, is treated by transplanting into the patient a stem cell or stem cell-hepatocyte doublet. To treat an inherited or acquired genetic or metabolic disease, a genetically-altered stem cell (singly or paired with a hepatocyte) is transplanted. For example, the stem cell may be transfected with DNA encoding Factor VIII:C, Factor IX, $\alpha_1$ antitrypsin, or low density lipoprotein receptor useful for treating human diseases such as hemophilia A and B, $\alpha_1$ antitrypsin deficiency, and familial hypercholesterolemia, respectively. Genetically-altered stem cells are useful as an in vivo recombinant protein delivery system and have the advantage of being capable of immortality (and thus, greater long-term survival) compared to differentiated cells, i.e., stem cells are capable of giving rise to differentiated progeny but retain the capacity for self-renewal.

The cells of the invention are also useful as the biological component of a perfusion device or as a source of functional differentiated hepatocytes which can then be used as the biological component of a perfusion device such as a liver assist device (LAD) or bioreactor. Contact of a patient-derived bodily fluid with the such hepatocytes results in detoxification of the bodily fluid for subsequently return to the patient.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described herein. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the detailed description, and from the claims.

BRIEF DESCRIPTION OF THE DRAWING

FIGS. 4A and 4B are photographs of the same cells in the same microscopic field. FIG. 4A shows CK19 staining, and FIG. 4B shows desmoplakin staining. Simultaneous double label immunofluorescence analysis shows that the stem cell (indicated with an arrow) expresses both CK19 and desmoplakin. The pattern of desmoplakin staining is continuous from the stem cell to the neighboring hepatocyte (denoted "H") indicating that the two cells were co-isolated and are joined by desmosomal junctions.

FIGS. 5A and 5B are photographs of the same cells in the same microscopic field. FIG. 5A is a view under phase microscopy, whereas FIG. 5B shows BrdU fluorescence.

Facultative liver stem cells

Figure 1:
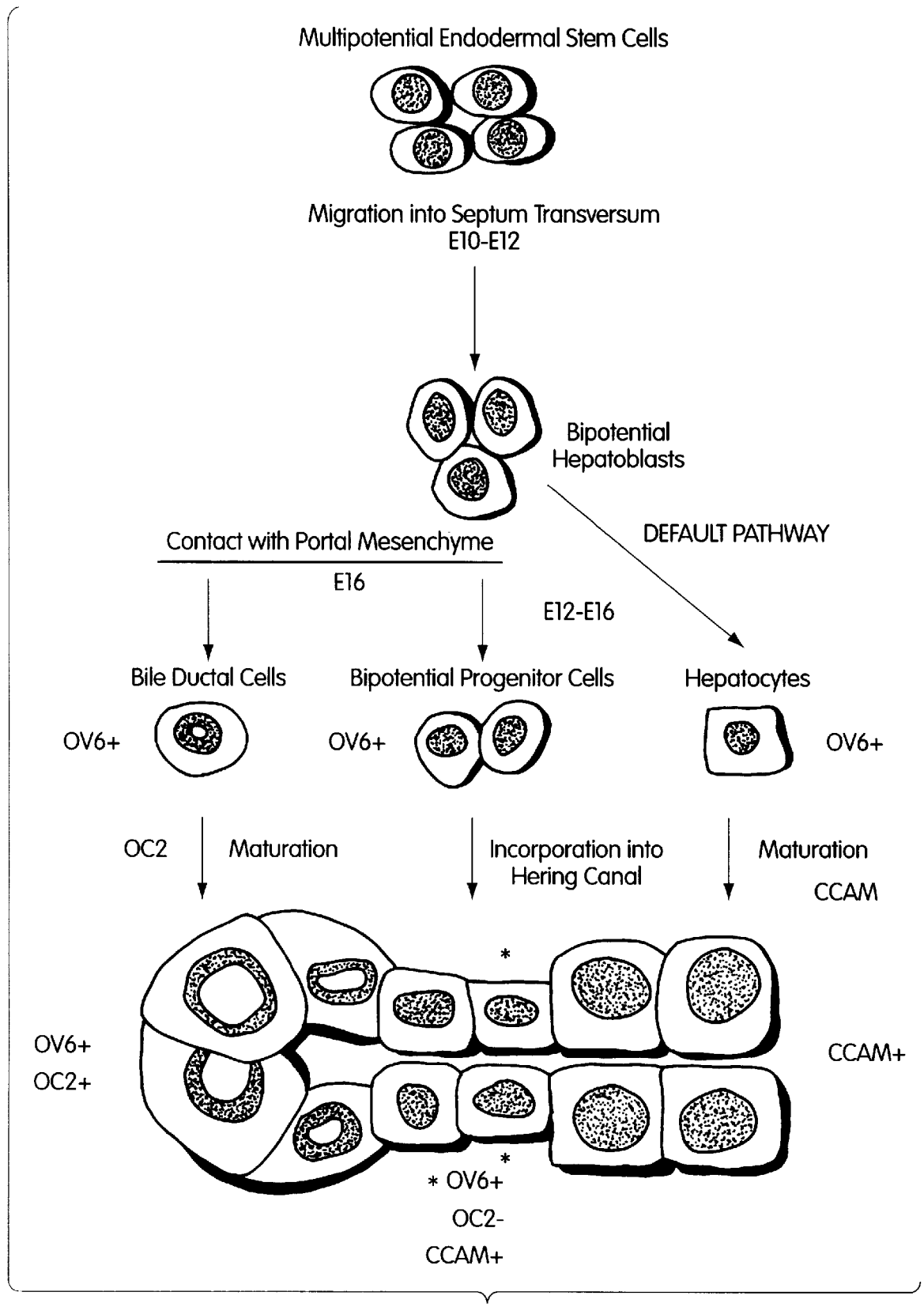
FIG. 1 is a diagram showing development of a liver stem cell.

The existence of a liver stem cell has been disputed for decades. Following hepatic injury that impairs the replicative capacity of hepatocytes, a heterogenous population of small stem-like cells called oval cells arises in the liver. Oval cells are small cells of the liver with oval nuclei which proliferate in response to exposure to carcinogens. Oval cells do not exist in normal liver tissue, but arise after a stressful stimulus such as a mechanical injury or exposure to a carcinogen. Activation of a stem cell compartment of the liver gives rise to a population of oval cells. Such oval cells are bipotential, i.e., they may differentiate into hepatocytes or bile ductal cells (FIG. 1).

Most attempts to isolate stem cells have been based on the expression of oval cell antigens, e.g., OV6, OC2, and OC3, by putative stem cells. However, these antigens may also be present on other liver cell types, e.g., bile duct cells or mesothelial cells, resulting in contamination of a preparation of putative stem cells with these other cell types. The invention identifies a novel phenotypic profile and solves the contamination problem by requiring isolation of a specific type of liver cell cluster, i.e., one characterized by a hepatocyte joined to a small non-hepatocytic cell via desmosomal junctions. Further isolation measures may include selection for expression of bile duct cell-specific antigens.

Oval cells are the progeny of the stem cells described herein. Although the stem cells of the invention share many cell markers with other liver cells, they are distinguished from oval cells and other putative stem cells by virtue of their tight association with a hepatocyte. This distinguishing characteristic allows identification and purification of a unique stem cell that upon proliferation gives rise to oval cells which differentiate into cells of hepatic lineage (rather than biliary lineage). The isolated stem cells (or cell clusters) can be used to repopulate a damaged liver, for gene therapy, and as the biological component of a liver assist device.

Preparation of liver stem cells and liver cell clusters

Liver tissue is enzymatically digested to dissociate cells from connective tissue while preserving the integrity of stem cell-hepatocyte clusters. In vivo, the stem cells reside in a unique niche of the liver, i.e., the canals of Hering, and stem cells derived from this niche are identified by their expression of one or more bile duct cell markers. Previous cell isolation protocols yielded single cell suspensions, whereas the method of the invention provides for isolation of cell clusters. Participation in a cell cluster represents a reliable distinguishing character of a pre-oval cell stem cell and is the only known marker of this cell type. Following enzymatic dissociation of the liver, the cell suspension is enriched for periportal hepatocytes associated with the biliary tree, and the cell suspension is subjected to enrichment for cell clusters, e.g., cell doublets, which contain a cell that expresses bile ductal antigens. For example, a suspension of rodent or human liver cells is subjected to selection for stem cells or clusters which express the marker CK19.

Mammalian organ donors may be used to provide liver tissue from which stem cells and doublets are isolated. For example, tissue is obtained from a rodent such as a mouse or rat, a dog, a baboon, a pig, or a human. The tissue is obtained from a deceased donor, an aborted fetus, or from a living donor, e.g., from a needle biopsy, a small wedge biopsy, or a partial hepatectomy. In some cases, autologous cells may be obtained from a patient, manipulated in vitro, e,g., to introduce heterologous DNA, and returned to the patient. More typically, the cells are obtained from a heterologous donor. If the donor hepatocytes are heterologous, then donor-recipient histocompatibility is determined. Class I and class II histocompatibility antigens are determined and individuals closely matched immunologically to the patient are selected as donors. All donors are screened for the presence of transmissible viruses (e.g., human immunodeficiency virus, cytomegalovirus, hepatitis A/B). Suitable donors are those which are free from the tested infectious diseases.

Rat liver tissue and human liver tissue (obtained from cadavers) were used as sources of tissue for the preparation of stem cells and cell clusters. Male Fisher rats were obtained from Charles River. Reagents and buffers are described below.

TABLE 1

| Reagent | Vendor | Catalog # | Concentration |
| --- | --- | --- | --- |
| DMEM-F12* | Gibco | 12400-086 | Stock |
| HBSS* | Gibco | 61200-093 | Stock |
| CMF* | Gibco | 21250-014 | Stock |
| HEPES | Sigma | H9136 | 0.1 M |
| CaCl2 | Sigma | C7902 | 500 mM |
| BSA | Intergen | 3225-75 | .4 mg/ml |
| STI | Gibco | 17075-029 | .1 mg/ml |
| Collagenase Type IV | Worthington | | 60 units/ml |
| BrdU | Sigma | B9285 | 150 mg/kg |
| Percoll | Pharmacia | 17089101 | 90% |
| Dynabeads | Dynal | 110.05 | $1 \times 10^7$ beads/ml |
| 2 AAF | Innovative Research of America | A-102 | 35 mg pellet (21 d release) |

Preperfusion buffer was prepared by mixing CMF (475 ml) with 0.1 M Hepes (25 ml of stock in which 23.83 g Hepes was dissolved in 990 ml dH20, pH to 7.0, QS to 1 L and filter sterilized). The digestion buffer used is formulated to liberate cells from the liver organ but to preserve the integrity of cell clusters (approximately 2–10 cells in size, optimally 2–3 cells in size) rather than to yield a suspension of single cells. Subjecting liver tissue to the digestion buffer described does not yield a single cell suspension, but a mixture of single cells and cell clusters, e.g., doublets or triplets, and single cells. The clusters are then retrieved and the single cells discarded.

The digestion buffer (Digestion Buffer I) contains Collagenase Type IV (60 units/ml). Digestion Buffer I (100 ml) contains Preperfusion buffer (250 ml), $CaCl_2$ 500 mM 100× stock (2.5 ml), STI (0.025 g), and Collagenase Type IV (60 units/ml). Digestion Buffer II is a solution of 0.02 g of BSA in 50 ml of Digestion Buffer I. The cell suspension buffer contains HBSS (475 ml) and 0.1 M Hepes (25 ml). The cell washing buffer contains DMEM-F12 (500 ml) and BSA (5 g). CMF, HBSS and DMEM-F12 are typically oxygenated for 5 minutes prior to adding other reagents. The pH of the preperfusion, suspension and washing buffers is adjusted to 7.2–7.3, the digestion buffer to 7.4–7.5. All buffers are filtered using 0.2 micron filter. The preperfusion, digestion and suspension buffers are used at 37° C., while the washing buffer is kept ice cold.

Male Fisher rats weighing between 115 g–170 g were anesthetized with Xylazine (10 mg/kg) and Ketamine (50 mg/kg). The inferior vena cava was canulated in the vicinity of the right renal vein, the aorta tied off, and the portal vein cut. The liver was perfused with preperfusion buffer at a flow rate of 20 ml/min. for approximately 4–5 mins., until the blood of the liver was cleared. Perfusion was then continued using Digestion Buffer at 30 ml/min. for approximately 6–8 min. The liver was excised, minced, and placed in a spinner flask with 100 ml of suspension buffer. The flask was placed in a 37° C. incubator on a stirring plate for 40–50 minutes. The combined suspension was sequentially filtered through a 230 micron steal mesh filter, and a 60 micron nylon mesh filter. The remnant remaining on the filters was washed off and placed in a 25 ml flask with 10 ml of digestion buffer II. The flask was placed in a 37° C. shaking water bath set to 160 shaker rate/min. After 20 minutes, the cell suspension was transferred to a 15 ml tube, and the suspension allowed to settle by gravity.

The supernatant and the remnant (settled material) were then separated. The supernatant was decanted and centrifuged at 80× g for 5 minutes. Fresh digestion buffer was added to the cells and placed back into the shaking water bath. The pellet remaining after the centrifugation was resuspended with washing buffer and kept on ice. If the cells appeared to be very adherent to the biliary tree, a solution of 1 mM EGTA dissolved in CMF was substituted for 5 minutes in place of a digestion step.

The cell suspension that was kept on ice, is then filtered through a 60 micron nylon mesh filter to remove large aggregates of cells and mixed with an equal volume of 90% Percoll and 10% 10× DMEM-F12. This is then centrifuged at 300× g for 5 minutes. The pellet was resuspended in washing buffer, and centrifuged at 120× g for 5 minutes. The pellet is then resuspended in washing buffer.

An immunosubstraction step is first carried out to remove undesired cells, thereby enriching for desired stem cell-hepatocyte clusters. Dynabeads were conjugated to a mouse monoclonal antibody specific for rat bile duct and mesothelial cells ($IgG_{2b}$). The beads were added to the cell suspension, and incubated at 4° C. on a rotator for 10 minutes. The suspension was then placed on a magnet to remove antibody-positive cells; these cells were discarded. This step was repeated 3 additional times. The antibody-negative cells were subjected to more incubations with Dynabeads conjugated to an antibody specific for CCAM (e.g., anti-rat cell-CAM 105; Endogen), and antibody-positive cells with a stem cell attached (e.g., cell clusters such as doublets and triplets) were cultured and cytospinned.

Isolated cell clusters containing a stem cell and a hepatocyte are further processed to achieve a population of isolated stem cells. For example, the sample of cells is trypsinized to dissociate the cell clusters, i.e., enzymatically disrupt the desmosomal junctions. Since hepatocytes are particularly sensitive to trypsin (or pronase), this step not only separates the cells but aids in removing the hepatocytes. The cell preparation is then subjected to further selection with antibodies specific for such cell markers as CK19 (Amersham), CCAM (Endogen), dipeptidyl peptidase-4 (Endogen) in combination with magnetic beads or FACS sorting to enrich for the desired stem cell. Antibodies to other markers such as γGT, VLA-2, VLA-3, VLA-5, or VLA-6 CEA may also be used.

Figure 2:
FIG. 2 is a photomicrograph of a liver cell doublet derived from normal adult rat liver tissue. The stem cell (indicated by an arrow) shows positive labelling with an antibody specific for the cell marker OV6. The stem cell and hepatocyte of the doublet a joined by desmosomal junctions.
Figure 3:
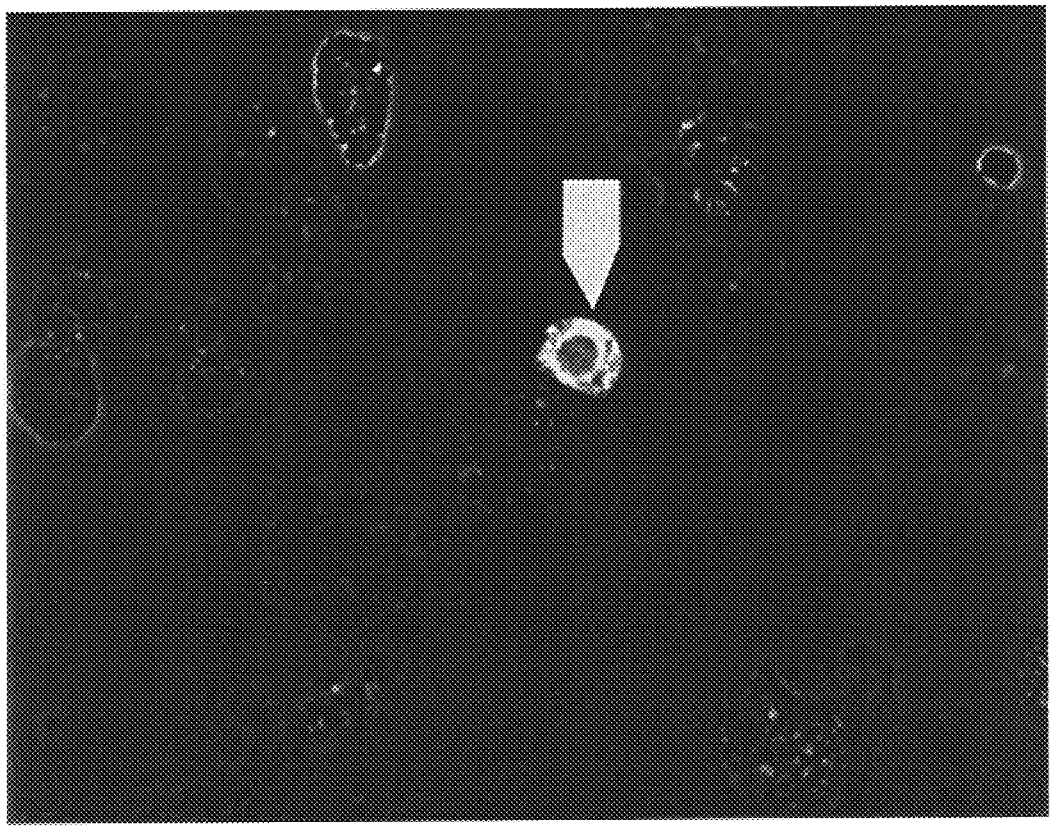
FIG. 3 is a photomicrograph of a liver cell doublet derived from normal adult human liver tissue. The stem cell (indicated by an arrow) shows positive labelling with an antibody specific for the cell marker CK19. The stem cell and hepatocyte of the doublet a tightly joined by desmosomal junctions.
Figure 4A:
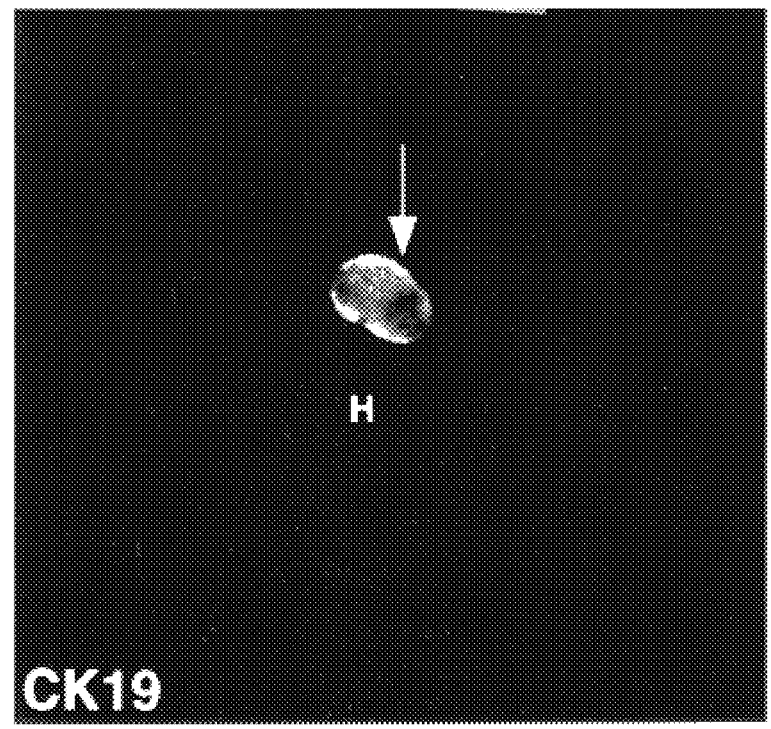
FIGS. 4A and 4B are photomicrographs of stem cell-hepatocyte cell doublets derived from rat liver tissue showing the tight association between the hepatocyte and the stem cell. The two cells of the cell doublet are joined by desmosomal junctions as demonstrated by positive staining with an antibody specific for desmoplakin, a component of the desmosomal junction.
Figure 4B:
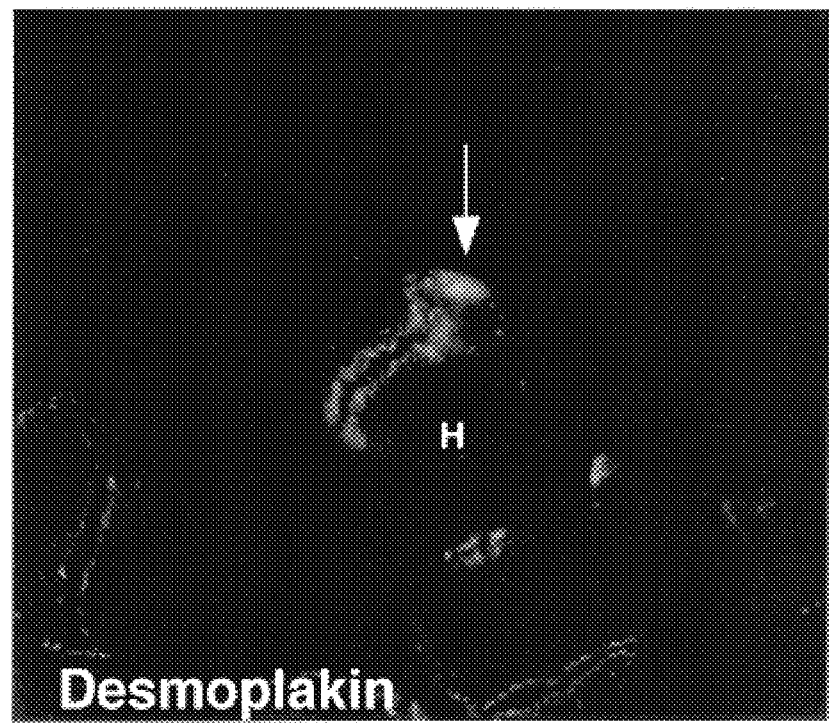

FIGS. 2 and 3 show an isolated stem cell-hepatocyte doublet derived from a normal rat liver and a normal human liver, respectively. In each figure, the smaller of the two cells (indicated with an arrow) is the stem cell. The rat stem cell of the doublet is also OV6-positive; the human stem cell is CK19-positive (antibodies for CK19 bind to both rat and human stem cells). The stem cell and hepatocyte of the doublet a joined by desmosomal junctions (FIGS. 4A and 4B).

Bioassay to Activate the Stem Cell Compartment

To confirm the identity of the stem cell isolated, proliferation of the stem cell compartment was carried out in vivo using a liver carcinogen and the stem cell-hepatocyte clusters isolated as described above. The proliferative capabilities were evaluated and the expression of cell markers measured.

Approximately 48 hours prior to stem cell isolation, male Fisher rats weighing between 115–170 g were anesthetized with metophane, and one pellet of the liver carcinogen 2-acetylaminofluorene (2-AAF) was placed in the peritoneal cavity of the animal. Alternatively, the carcinogen pellet was left in the animal for 2 weeks prior to administration of a radioisotope (to measure cell proliferation) and subsequent sacrifice for retrieval of stem cells.

Cellular incorporation of bromouridine (BrdU) was used as a measure of cell proliferation. An hour after surgery, a dose of BrdU was dissolved in normal saline is injected intraperitoneally. Additional doses were given 4 and 22 hours later.

Rats were sacrificed and perfusion of the liver was commenced 2 hours after the last dose of BrdU was administered. Cell clusters were isolated as described above. Cell suspensions enriched for stem cell-hepatocyte doublets were further subjected to selection for doublets expressing CCAM and analyzed for expression of cell markers and proliferation.

Figure 5A:
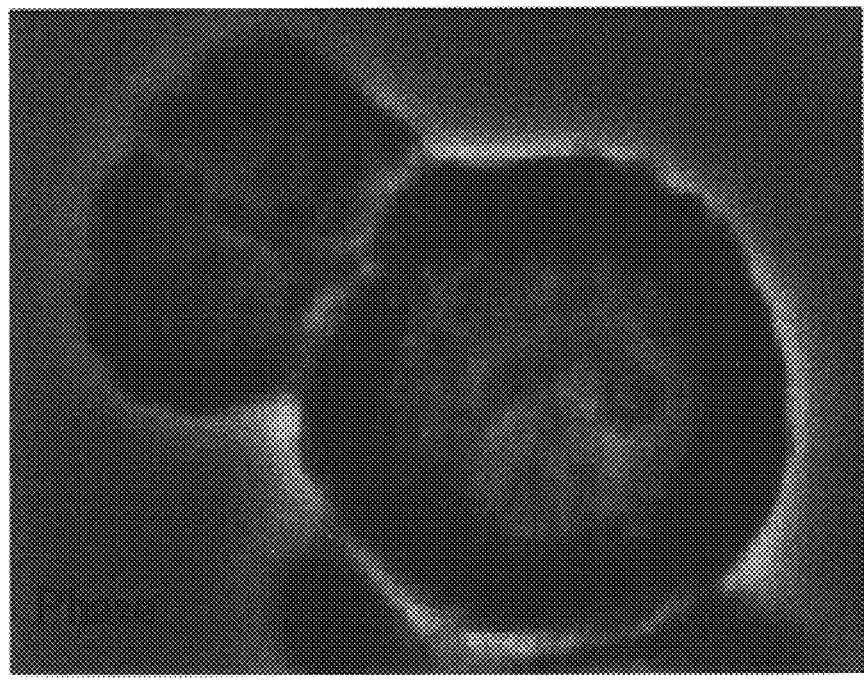
FIGS. 5A and 5B are photomicrographs of two stem cells attached to a hepatocyte. The cell cluster was derived from rat liver tissue.
Figure 5B:
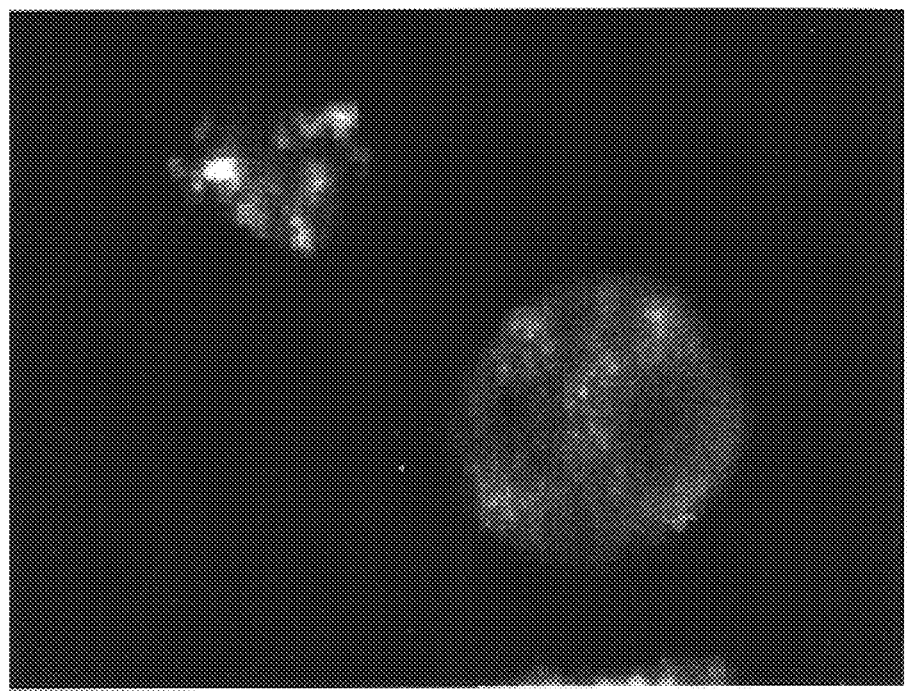

FIGS. 5A and 5B show a stem cell-hepatocyte triplet in which two OV6-positive stem cells are attached to a hepatocyte. One of the attached stem cells is strongly labelled with BrdU, indicating an actively proliferating cell. These results confirm that the small cell attached to a hepatocyte via desmosomal junctions is a liver stem cell.

Therapeutic Use

Stem cells and cell clusters are transplanted into individuals to treat a variety of pathological states including degenerative liver disease or disease characterized by production of a mutated protein or aberrant regulation of a non-mutated, i.e., normal, protein. The latter category of diseases include familial hypercholesterolemia, $\alpha_1$-antitrypsin deficiency, factor VIII deficiency (Hemophilia A) and factor IX deficiency (Hemophilia B)(see, e.g., Wilson et al., *Principles of Internal Medicine,* McGraw-Hill, N.Y., 1991)

Familial hypercholesterolemia is an autosomal dominant disorder in human patients caused by a deficiency of the receptor that mediates the uptake of low density lipoprotein (see, e.g., Scriver et al. (eds) *The Metabolic Basis of Inherited Disease,* McGraw-Hill, NY, pp 1215–1250). The disease leads to elevated levels of serum cholesterol and premature development of coronary artery disease.

Alpha$_1$-antitrypsin deficiency is a hereditary disorder characterized by reduced serum levels of $\alpha_1$-antitrypsin, a protease inhibitor that provides the major defense for the lower respiratory tract against destructive proteases. Children homozygous for $\alpha_1$-antitrypsin deficiency will develop significant liver disease including neonatal hepatitis and progressive cirrhosis, and $\alpha_1$-antitrypsin deficiency adults can lead to asymptomatic cirrhosis.

Hemophilia A and hemophilia B are sex-linked inherited plasma coagulation disorders due to defects in factors VIII and factor IX, respectively. Previous treatments for hemophilia A involved administration of plasma products enriched for factor VIII. Treatment of affected patients with stem cells genetically-altered to produce recombinant clotting factors avoids the potential risk of exposing patients to viral contaminants, such as viral hepatitis and human immunodeficiency virus (HIV).

Cell transplantation

Stem cells or cell doublets (either as is or genetically-altered to produce a recombinant gene product) are introduced into an individual in need of a hepatic transplant or in need of the protein encoded by the genetically-altered cell. In addition to using the cells for treatment of degenerative liver disease, stem cells can be administered to cancer patients who have undergone chemotherapy to kill cancerous liver cells. Thus, after administration of the chemotherapeutic agent, the patient's liver can be "reseeded" with stem cells.

If the cells are derived from heterologous, concomitant immunosuppression therapy is typically administered, e.g., administration of the immunosuppressive agent cyclosporine or FK506. Alternatively, the cells can be encapsulated in a membrane which permits exchange of fluids but prevents cell/cell contact. Transplantation of microencapsulated cells is known in the art, e.g., Balladur et al., 1995, Surgery 117:189–194; and Dixit et al., 1992, Cell Transplantation 1:275–279.

The cells may be introduced directly to the liver, e.g., via the portal vein, or deposited within other locations throughout the body, e.g., the spleen, pancreas, or on microcarrier beads in the peritoneum. For example, $10^2$ to $10^9$ cells are transplanted in a single procedure, and additional transplants are performed as required.

Differentiation of the stem cells is induced by contact with liver tissue, i.e., other hepatocytes or cell matrix components. Optionally, a differentiating agent may be co-administered or subsequently administered to the patient to promote stem cell differentiation.

Genetically-altered stem cells

Genetically-altered stem cells are useful to produce therapeutic recombinant proteins in vivo. The stem cells are isolated from a donor (nonhuman or human), transfected or transformed with a recombinant gene in vitro, and transplanted into the recipient. The genetically-altered stem cells produce the desired recombinant therapeutic protein in vivo leading to clinical improvement of the patient so treated.

Conventional gene transfer methods are used to introduce DNA into cells. The precise method used to introduce a replacement gene, e.g., clotting factor or metabolic protein is not critical to the invention. For example, physical methods for the introduction of DNA into cells include microinjection and electroporation. Chemical methods such as coprecipitation with calcium phosphate and incorporation of DNA into liposomes are also standard methods of introducing DNA into mammalian cells. DNA is introduced using standard vectors, such as those derived from murine and avian retroviruses (see, e.g., Gluzman et al., Viral Vectors, Cold Spring Harbor Laboratory, Cold Spring Harbor, N.Y., 1988). Standard recombinant DNA methods are well known in the art (see, e.g., Ausubel et al., *Current Protocols in Molecular Biology,* John Wiley & Sons, New York, 1989), and viral vectors for gene therapy have been developed and successfully used clinically (Rosenberg, et al., *N. Engl. J. Med,* 323:370 1990).

Liver Assist Devices

The stem cells, cell clusters, and progeny thereof are useful as the biological components of detoxification devices such as liver perfusion or liver assist devices.

A conventional liver assist device includes a rigid, plastic outer shell and hollow semi-permeable membrane fibers which are seeded with stem cells, cell doublets, or differentiated hepatocytes derived from the stem cells or cell clusters. Differentiation of stem cells is induced by contacting the cells with known differentiating factors, e.g., dimethylsulfoxide (DMSO), Vitamin A, sodium butyrate, or matrix components such as heparin sulfate.

The fibers may be treated with collagen, lectin, laminin, or fibronectin, for the attachment of cells or left untreated. Bodily fluid is perfused through the device for detoxification according to well known procedures and then returned to the patient.

Other embodiments are within the following claims.

What is claimed is:

1. An isolated liver cell cluster of less than 10 cells comprising a liver stem cell and a hepatocyte, wherein said stem cell does not express OC2.

2. The liver cell cluster of claim 1, wherein said liver cell cluster is a cell doublet.

3. The liver cell cluster of claim 1, wherein said hepatocyte and said stem cell are joined by a desmosomal junction.

4. The liver cell cluster of claim 1, wherein said stem cell is a pre-oval cell.

5. The liver cell cluster of claim 1, wherein said stem cell expresses OV6.

6. The liver cell cluster of claim 1, wherein said stem cell expresses a bile duct cell marker.

7. The liver cell cluster of claim 6, wherein said bile ductal cell marker is a cytokeratin.

8. The liver cell cluster of claim 7, wherein said cytokeratin is cytokeratin 19.

9. The liver cell cluster of claim 3, wherein said stem cell expresses desmoplakin.

10. The liver cell cluster of claim 6, wherein said stem cell is further characterized as expressing an antigen selected from the group consisting of laminin, desmoplakin I, cell-cell adhesion molecule (CCAM), carcinoembryonic antigen (CEA), dipeptidyl peptidase-4, γ-glutamyl transpeptidase (γGT), Very Late After Activation (VLA)-2, VLA-3, VLA-5, and VLA-6.

11. The liver cell cluster of claim 1, wherein said cluster is derived from adult liver tissue.

12. The cluster of claim 1, wherein said cluster is derived from a fetal or pediatric liver.

13. The liver cell cluster of claim 1, wherein said cluster is derived from human liver tissue.

14. The liver cell cluster of claim 1, wherein said cluster is derived from rodent liver tissue.

15. The liver cell cluster of claim 1, wherein said stem cell is multipotential.

16. The liver cell cluster of claim 1, wherein said stem cell comprises DNA encoding a heterologous polypeptide.

17. The liver cell cluster of claim 16, wherein said polypeptide is selected from the group consisting of ornithine transcarbamylase, arginosuccinate synthetase, glutamine synthetase, glycogen synthetase, glucose-6-phosphatase, succinate dehydrogenase, glucokinase, pyruvate kinase, acetyl Co A carboxylase, fatty acid synthetase, alanine aminotransferase, glutamate dehydrogenase, ferritin, low density lipoprotein (LDL) receptor, alcohol dehydrogenase, albumin, transferrin, complement component C3, α2-macroglobulin, fibrinogen, Factor XIII:C, Factor IX, or α1-antitrypsin.

18. A primary liver stem cell wherein said stem cell is obtained from normal liver tissue, and does not express OC2.

19. The stem cell of claim 18, wherein said liver cell cluster is a cell doublet.

20. The stem cell of claim 18, wherein said hepatocyte and said stem cell are joined by a desmosomal junction.

21. The stem cell of claim 18, wherein said stem cell is a pre-oval cell.

22. The stem cell of claim 18, wherein said stem cell expresses OV6.

23. The stem cell of claim 18, wherein said stem cell expresses a bile duct cell marker.

24. The stem cell of claim 23, wherein said bile 2 ductal cell marker is a cytokeratin.

25. The stem cell of claim 24, wherein said cytokeratin is cytokeratin 19.

26. The stem cell of claim 20, wherein said stem cell expresses desmoplakin.

27. The stem cell of claim 23, wherein said cell is further characterized as expressing an antigen selected from the group consisting of laminin, desmoplakin I, CCAM, CEA, dipeptidyl peptidase-4, γGT, VLA-2, VLA-3, VLA-5, and VLA-6.

28. The stem cell of claim 18, wherein said stem cell is derived from adult liver tissue.

29. The stem cell of claim 18, wherein said stem cell is derived from a fetal or pediatric liver.

30. The stem cell of claim 18, wherein said stem cell is derived from human liver tissue.

31. The stem cell of claim 18, wherein said stem cell is derived from rodent liver tissue.

32. The stem cell of claim 18, wherein said stem cell is multipotential.

33. The stem cell of claim 18, wherein said stem cell comprises DNA encoding a heterologous polypeptide.

34. The stem cell of claim 33, wherein said polypeptide is selected from the group consisting of ornithine transcarbamylase, arginosuccinate synthetase, glutamine synthetase, glycogen synthetase, glucose-6-phosphatase, succinate dehydrogenase, glucokinase, pyruvate kinase, acetyl CoA carboxylase, fatty acid synthetase, alanine aminotransferase, glutamate dehydrogenase, ferritin, LDL receptor, alcohol dehydrogenase, album transferrin, complement component C3, α2-macroglobulin, fibrinogen, Factor XIII:C, Factor IX, or α1-antitrypsin.

35. A method of obtaining an isolated liver stem cell comprising
   (a) isolating a liver cell cluster of less than 10 cells from normal liver tissue, said cluster comprising an OC2-negative stem cell associated with a hepatocyte;
   (b) dissociating said stem cell from said hepatocyte; and
   (c) removing said hepatocyte from said cluster to yield a liver stem cell.

36. The method of claim 35, comprising the step of enriching for periportal hepatocytes associated with the biliary tree.

37. The method of claim 35, wherein said liver cell cluster is a cell doublet.

38. The method of claim 35, wherein said liver cell cluster is derived from the canal of Hering of an adult liver.

39. The method of claim 35, further comprising selecting for expression of desmoplakin.

40. The method of claim 35, further comprising selecting for expression of OV6.

41. The method of claim 35, further comprising selecting for a cell which expresses an antigen selected from the group consisting of laminin, desmoplakin I, CCAM, CEA, dipeptidyl peptidase-4, γGT, VLA-2, VLA-3, VLA-5, and VLA-6.

42. The method of claim 35, further comprising after step (c) selecting for expression of desmoplakin.

43. The method of claim 35, further comprising after step (c) selecting for expression of OV6.

44. The method of claim 35, further comprising after step (c) selecting for a cell which expresses an antigen selected from the group consisting of laminin, desmoplakin I, CCAM, CEA, dipeptidyl peptidase-4, γGT, VLA-2, VLA-3, VLA-5, and VLA-6.

45. A primary liver stem cell, wherein said stem cell
   (a) expresses OV6, and
   (b) does not express OC2.

46. The stem cell of claim 45, wherein said stem cell expresses a bile duct cell marker.

47. The stem cell of claim 46, wherein said bile ductal cell marker is a cytokeratin.

48. The stem cell of claim 47, wherein said cytokeratin is cytokeratin 19.

49. The stem cell of claim 45, wherein said stern cell expresses desmoplakin.

50. The stem cell of claim 45, wherein said cell is further characterized as expressing an antigen selected from the group consisting of laminin, desmoplakin I, CCAM, CEA, dipeptidyl peptidase-4, γGT, VLA-2, VLA-3, VLA-5, and VLA-6.

* * * * *

UNITED STATES PATENT AND TRADEMARK OFFICE
CERTIFICATE OF CORRECTION

PATENT NO. : 6,129,911  
APPLICATION NO. : 09/113774  
DATED : October 10, 2000  
INVENTOR(S) : Ronald A. Faris Page 1 of 1

It is certified that error appears in the above-identified patent and that said Letters Patent is hereby corrected as shown below:

Please insert the following paragraph at column 1, line 2, after the title:

--STATEMENT AS TO FEDERALLY SPONSORED RESEARCH
This invention was made with U.S. government support under United States NIH Grant No. R01-CA66005. The United States Government has certain rights in the invention.--

Signed and Sealed this

Fourteenth Day of November, 2006

JON W. DUDAS  
*Director of the United States Patent and Trademark Office*